United States Patent [19]
Dykstra

[11] Patent Number: 4,759,377
[45] Date of Patent: Jul. 26, 1988

[54] APPARATUS AND METHOD FOR MECHANICAL STIMULATION OF NERVES

[75] Inventor: Dennis D. Dykstra, Eagan, Minn.

[73] Assignee: Regents of the University of Minnesota, Minneapolis, Minn.

[21] Appl. No.: 935,267

[22] Filed: Nov. 26, 1986

[51] Int. Cl.[4] ............................................... A61B 5/04
[52] U.S. Cl. ..................................... 128/733; 128/740
[58] Field of Search .............. 128/739, 740, 744, 733, 128/54, 55, 737, 741, 782; 200/61.85

[56] References Cited

U.S. PATENT DOCUMENTS 3,344,781 10/1967 Allen ..................................... 128/739
3,515,125 6/1970 Ruskin .................................. 128/740

FOREIGN PATENT DOCUMENTS 195038 11/1967 U.S.S.R. .............................. 128/740

OTHER PUBLICATIONS

Aminoff, "Electromyography in Clinical Practice", Addison Wesley Publishing Co., 1978, Ch. 4.
Frollo et al., Medical and Biological Engineering and Computing, vol. 19, No. 6, Nov. 1981, Microprocessor-based instrument for Achilles tendon reflex measurements".
Yamada et al., "An Automated Measuring System for EMG Silent Period", IEEE Transactions in Biomedical Engineering, vol. BME 27, No. 7, Jul. 1980.

Primary Examiner—William E. Ramm
Assistant Examiner—Timothy G. Philips
Attorney, Agent, or Firm—Merchant, Gould, Smith, Edell, Welter & Schmidt

[57] ABSTRACT

An improved method and apparatus for mechanical stimulation of nerves to evoke reflexive response, particularly sacral reflex latentency, comprises a hammer (30) having opposite distal and proximal ends. A normally open switch (36) with an extending switch arm (38) is mounted on the distal end of the handle (32) and positioned to close upon impact. The switch (36) is adapted for connection to an electromyograph. The switch (36) is preferably partially recessed within an enlargement (40) of the distal end of the handle (32). The switch (36) closes in response to tapping on the patient with the hammer (30) to effect manual stimulation and trigger recording of the reflexive response sensed via an electrode (26).

5 Claims, 1 Drawing Sheet

U.S. Patent        Jul. 26, 1988        4,759,377
FIG. 1
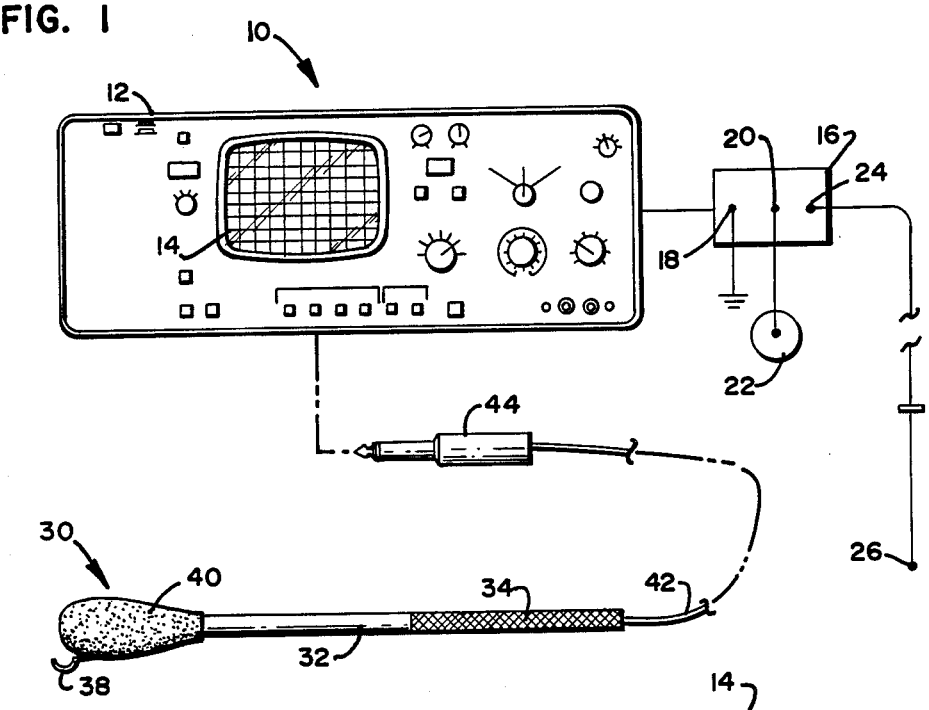
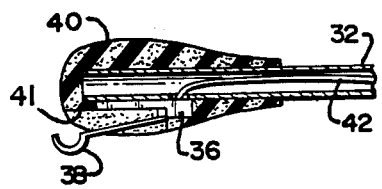
FIG. 2
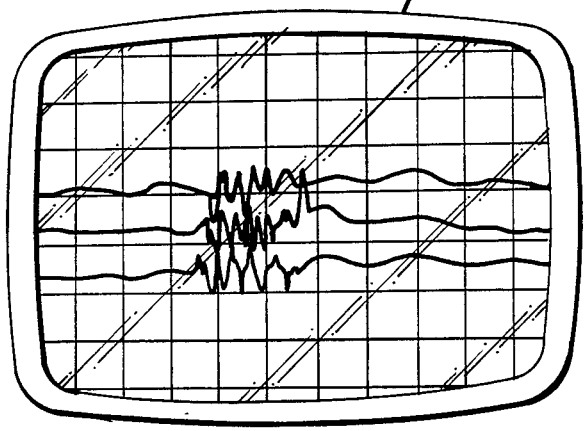
FIG. 3

4,759,377

APPARATUS AND METHOD FOR MECHANICAL STIMULATION OF NERVES

TECHNICAL FIELD

The present invention relates generally to a nerve stimulator. More particularly this invention pertains to a technique for mechanical stimulation of the pudendal nerve for use in conjunction with an electromyograph to evoke, record and measure sacral reflex latency.

BACKGROUND ART

In urodynamic studies, the sacral reflex latency is used to examine certain spinal cord segments by stimulation of the pudendal nerve. The basic reflex arc from the glans penis or clitoris to the external urethral sphincter is believed to be from sensory fibers in the pudendal nerve to sacral cord internuncial neurons to motor fibers in the pelvic splanchnic nerve to skeletal muscle fibers in the external urethral sphincter. It has been suggested that the sacral reflex closely resembles the blink and other flexor reflexes derived from cutaneous receptors.

The sacral reflex has traditionally been obtained by use of electromyographic recording electrodes and electrical stimulation of the pudendal nerve. A bipolar electrode is applied to the glans penis or clitoris, followed by delivery of periodic electrical stimuli at gradually increasing intensities until a consistent reflex of the shortest latency is sensed via a monopolar needle electrode in the external urethra sphincter. As the electrical stimuli are administered, the responses are stored on the screen of the electromyograph for measurement and evaluation.

Due to the sensitivity of the area being stimulated, it will be appreciated that electrical stimulation to evoke this reflex can be quite uncomfortable for many patients, especially children, and can make it difficult or impossible to detect the reflex in patients with low pain thresholds. The apprehension, pain and discomfort actually can make the components of a flexor reflex more difficult to obtain. Further, stimulus artifact may occur when the electrical technique is used which can create problems in obtaining the sacral reflex, especially in women and children. Although mechanical stimulation has been applied previously in connection with evaluation of other physiocological responses, the technique of mechanical stimulation has not been used heretofor in determining sacral reflex latencies.

A need has thus arisen for an improved non-electrical method and apparatus for stimulating the pudendal nerve to determine sacral reflex latencies without the apprehension, pain and discomfort associated with the prior techniques.

SUMMARY OF THE INVENTION

The present invention comprises a mechanical apparatus and method for stimulating the pudendal nerve which overcomes the foregoing difficulties and other problems associated with the prior art. In accordance with the invention, there is provided a new technique incorporating mechanical stimulation to obtain the sacral reflex latency. The invention herein includes a mechanical response hammer comprising an elongate handle having opposite distal and proximal ends. A normally open switch is mounted on the distal end of the handle, which is preferably enlarged and weighted. The switch is electrically connected to the stimulate output of an electromyograph. A monopolar needle electrode, which is placed in the external urethral sphincter, is electrically connected to the input of the electromyograph. As the glans penis or clitoris is tapped with the hammer, the switch thereon closes to trigger timed sweeps on the screen of the electromyograph and record the reflex response sensed by the monopolar needle electrode.

BRIEF DESCRIPTION OF DRAWINGS

A better understanding of the invention can be had by reference to the following Detailed Description in conjuction with the accompanying drawing, wherein:

FIG. 1 is an illustration of a system incorporating the mechanical nerve response hammer of the invention;

FIG. 2 is an enlarged partial section view of one end of the mechanical nerve response hammer; and FIG. 3 is an illustration of some tracings of the response evoked with the invention.

DETAILED DESCRIPTION

Referring now to the drawing, wherein like reference numerals designate like or corresponding elements throughout the views, and particularly referring to FIG. 1, there is shown a system 10 for obtaining nerve response such as the sacral reflex. Although system 10 is particularly adapted for determining sacral reflex latencies by stimulation of the pudendal nerve, it will be understood that the invention could be used for stimulation of other nerves. System 10 includes a conventional two-channel electromyograph 12 having an ociloscope screen 14 and other associated controls, jacks, etc. For example, a model M two-channel machine from Teca Corporation of Pleasantville, N.Y., can be used for the electromyograph 12. A preamplifier 16 is connected to the input of the electromyograph 12. The preamplifier 16, which is also of conventional construction, includes a ground terminal 18, a reference terminal 20 connected to a skin sensor or electrode 22, and an active terminal 24 connected to a monopolar needle electrode 26. The electrode 22 is attached to the skin of the patient to provide a reference voltage. The electrode 26 is inserted into the external urethral sphincter of the patient to sense the sacral response. In contrast to the prior art, and as will be explained more fully hereinafter, the system 10 incorporates a mechanical response hammer 30 instead of an electrical stimulator to evoke the sacral reflex latency.

Referring now to FIG. 1 in conjunction with FIG. 2, the mechanical response hammer 30 includes an elongate handle 32 having opposite distal and proximal ends. The handle 32 can comprise a straight hollow tube about 20 centimeters long. Knurling 34 can be provided on the proximal end of the tube 32 to faciliate manipulation by the doctor. A normally open switch 36 is mounted on the distal end of tube 32. The switch 36 includes an extending switch arm 38.

In accordance with the preferred construction, the distal end of the handle 32 is weighted and the switch 36 is partially recessed within a smooth enlargement 40 with switch arm 38 extending beyond notch 41 in the enlargement. The switch 36 is electrically connected via line 42 and plug 44 to the stimulate output on the electromyograph 12.

To obtain the sacral reflex latency with system 10, the electromyograph 12 is energized and the electrodes 26 and 22 are connected to the patient. The electrode 26 is placed in the external urethral sphincter of the patient. The glans penis or clitoris is then tapped several times with the hammer 30 to evoke, record, and measure the sacral reflex latency. The taps are preferably spaced about 2 seconds apart. The switch 36 closes with each tap to trigger a sweep on the ocilloscope screen 14 which also records and stores the reflex response sensed by electrode 26. Closure of switch 36 thus occurs simultaneously with mechanical stimulation of the nerve upon impact of the hammer 30. FIG. 3 illustrates three sample tracings of mechanically evoked sacral responses in a patient by means of the system 10 of the invention. Each horizontal unit represents 10 milliseconds and each vertical unit represents 200 microvolts.

From the foregoing, it will be appreciated that the present invention comprises an improved nerve stimulator having several advantages over the prior art. The mechanical response hammer avoids the apprehension, discomfort and pain associated with the electrical stimulators of the prior art, which in turn facilitates determining sacral reflex latencies. Other advantages will be evident to those skilled in the art.

Although particular embodiments of the invention have been illustrated in the accompanying drawing and described in the foregoing Detailed Description, it will be understood that the invention is not limited only to the embodiments disclosed, but is intended to embrace any alteratives, equivalents, modifications and/or rearrangements of elements falling within the scope of the invention as defined by the following claims.

What is claimed:

1. Apparatus for mechanically stimulating the pudendal nerve in order to record sacral reflex response on an electromyograph, which comprises:
   an elongate, straight handle having opposite distal and proximal ends;
   a smooth, weighted enlargement covering the distal end of said handle;
   the proximal end of said handle being knurled to facilitate manipulation;
   a normally open switch mounted on the distal end of said handle, recessed within said enlargement, said switch including a switch arm extending outwardly through a notch in said enlargement and positioned to close upon impact thereof; and
   means for electrically connecting said switch to the electromyograph.

2. A system for mechanically evoking, electrically recording, and measuring pudendal nerve response, which comprises:
   an electromyograph having an oscilloscope screen, an input, and an output;
   a first electrode for connection to the skin of a patient for providing a reference signal;
   a second electrode for connection to the external urethral sphincter of the patient for providing a sacral reflex signal;
   a preamplifier connected between said first and second electrodes and the input of said electromyograh; and
   mechanical means for selectively stimulating the pudendal nerve of the patient, including:
     an elongate, straight handle having opposite distal and proximal ends;
     a smooth, weighted enlargement covering the distal end of said handle;
     the proximal end of said handle being knurled to facilitate manipulation;
     a normally open switch mounted on the distal end of said handle, recessed within said enlargement, said switch including a switch arm extending through a notch in said enlargement and positioned to close upon impact thereof; and
     means for electrically connecting said switch to the output of said electromyograph in order to trigger a timed sweep of the oscilloscope screen upon mechanical stimulation of the pudendal nerve and thus record the response sensed by said second electrode.

3. the apparatus of claim 2, wherein said handle is tubular, and said electrical connection means includes a lead extending through said handle and out the proximal end thereof.

4. A method for determining sacral reflex latency in a patient, comprising the steps of:
   providing an electromyograph with a display;
   connecting a first electrode to the patient to provide a reference signal;
   connecting a second electrode to the external urethral sphincter of the patient to sense response and generate a reflex signal, said electromyograph being responsive to said first and second electrodes;
   selectively mechanically stimulating the pudendal nerve of the patient; and
   triggering timed sweeps of the display in said electromyograph upon mechanical stimulation to record the reflexive response sensed by said second electrode on the electromyograph.

5. The method of claim 4, wherein the step of selectively mechanically stimulating the pudendal nerve of the patient is accomplished by:
   providing an elongate handle having opposite distal and proximal ends;
   mounting a normally open switch with a projecting switch arm on the distal end of the handle;
   connecting the switch to the output of the electromyograph; and
   tapping the pudendal nerve of the patient with the distal end of said handle to effect mechanical stimulation and simultanously trigger timed movement of the display in the electromyograph.

* * * * *